US007648829B2

(12) United States Patent
Alderete et al.

(10) Patent No.: US 7,648,829 B2
(45) Date of Patent: *Jan. 19, 2010

(54) **METHOD AND DEVICE FOR *TRICHOMONAS* DETECTION**

(75) Inventors: John P. Alderete, Palo Alto, CA (US); Paul C. Castella, San Francisco, CA (US)

(73) Assignee: Xenotope Diagnostics, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/931,488

(22) Filed: Oct. 31, 2007

(65) Prior Publication Data

US 2008/0268466 A1 Oct. 30, 2008

Related U.S. Application Data

(63) Continuation of application No. 10/112,410, filed on Mar. 30, 2002, now Pat. No. 7,291,477.

(60) Provisional application No. 60/302,733, filed on Jul. 3, 2001.

(51) Int. Cl.
*G01N 33/554* (2006.01)

(52) U.S. Cl. .................. 435/7.32; 436/514; 436/518; 436/524; 436/525; 436/528; 436/531; 435/287.1; 435/287.9; 435/7.1; 422/55; 422/56; 422/58; 422/61

(58) Field of Classification Search ............... 436/514, 436/518, 524, 525, 528, 531; 435/287.1, 435/287.9, 7.1, 7.32; 422/55, 56, 58, 61
See application file for complete search history.

(56) References Cited

U.S. PATENT DOCUMENTS

| 4,514,498 | A | 4/1985 | Kettman et al. |
|---|---|---|---|
| 4,707,442 | A | 11/1987 | Alderete |
| 4,861,711 | A | 8/1989 | Friesen et al. |
| 5,004,694 | A | 4/1991 | Moay et al. |
| 5,037,615 | A | 8/1991 | Kane |
| 5,330,897 | A | 7/1994 | Pindak et al. |
| 5,369,005 | A | 11/1994 | Baseman et al. |
| 5,415,994 | A | 5/1995 | Imrich et al. |
| 5,516,638 | A | 5/1996 | Urnovitz et al. |
| 5,679,551 | A | 10/1997 | Alderete |
| 5,741,662 | A | 4/1998 | Madsen et al. |
| 5,776,694 | A | 7/1998 | Sheiness et al. |
| 5,876,985 | A | 3/1999 | Alderete |
| 5,879,881 | A | 3/1999 | Rubenstein |
| 5,922,563 | A | 7/1999 | Alderete |
| 6,063,905 | A | 5/2000 | Capra et al. |
| 6,174,293 | B1 | 1/2001 | Buck et al. |
| 6,207,395 | B1 | 3/2001 | Valkirs et al. |
| 6,528,321 | B1 | 3/2003 | Fitzgerald et al. |
| 6,766,817 | B2 | 7/2004 | da Silva |
| 6,824,975 | B2 | 11/2004 | Hubscher et al. |
| 6,918,404 | B2 | 7/2005 | da Silva |
| 7,066,586 | B2 | 6/2006 | da Silva |
| 7,244,398 | B2 | 7/2007 | Kotary et al. |
| 7,270,995 | B2 | 9/2007 | Matsushita et al. |
| 7,285,255 | B2 | 10/2007 | Kadlec et al. |
| 2002/0045195 | A1 | 4/2002 | Hubscher et al. |
| 2003/0032029 | A1 | 2/2003 | Collins |
| 2003/0073147 | A1 | 4/2003 | Alderete et al. |
| 2008/0015531 | A1 | 1/2008 | Hird et al. |

FOREIGN PATENT DOCUMENTS

| EP | 0 050 424 B1 | 4/1982 |
|---|---|---|
| EP | 0810436 A1 | 12/1997 |
| WO | WO 92/07096 A1 | 4/1992 |

OTHER PUBLICATIONS

Estrada et al. "Reporting and Concordance of Methodologic Criteria Between Abstracts and Articles in Diagnostic Test Studies" *JGIM* 15:183-187 (2000).
European Search Report for EP 03746064.9; dated Mar. 22, 2007.
Genzyme Diagnostics Product Information Sheet for OSOM Trichomonas Rapid Test. Printed from Genzyme website, Apr. 2007.
Huppert et al. "Use of an immunochromatographic assay for rapid detection of *Trichomonas vaginalis* in vaginal samples" *J. Clin. Microbiol.* 43(2):684-687 (2005).
Miller et al. "Assessment of a rapid antigen detection system for *Trichomonas vaginalis* infection" *Clinical and Diagnostic Laboratory Immunology* 10(6):1157-8 (2003).
Mohamed et al. "Urine proves a poor specimen for culture of *Trichomonas vaginalis* in women" *Sex. Transm. Infect.* 77(1):78-79 (2001).
Patel et al. "Systematic Review of Diagnostic Tests for Vaginal Trichomoniasis" *Infectious Diseases in Obstetrics and Gynecology* 8:248-257 (2000).
Planned Parenthood Report "XenoStrip™-Tv *Trichomonas* Test Clinical Efficacy Assessment" Xenotope Diagnostics, Inc. Jan. 25, 2004.
Rappelli et al. "Sequence of cDNA coding for a 65 kDa adhesive protein for the specific detection of *Trichomonas vaginalis* by PCR" *FEMS Microbiology Letters* 129:21-26 (1995).

(Continued)

*Primary Examiner*—Jennifer E Graser
(74) *Attorney, Agent, or Firm*—Myers Bigel Sibley & Sajovec, P.A.

(57) ABSTRACT

A method and kit for detecting *Trichomonas vaginalis* infection in a human subject are disclosed. In the method, a body-fluid sample such as a vaginal-swab sample or urine is obtained from the subject and contacted with an antibody specific against a *Trichomonas* adhesin peptide, forming an antibody-adhesin peptide complex if the subject is infected with *Trichomonas*. The presence or absence of the complex establishes, with a reliability of at least 80%, in the case of a vaginal swab sample, and with a reliability of at least 40% in the case of a urine sample, the presence or absence, respectively, of *Trichomonas* infection in the subject. A preferred test kit employs a dry-strip, sandwich assay, format.

2 Claims, 2 Drawing Sheets

OTHER PUBLICATIONS

Stary et al. "Detection of *Trichomonas vaginalis* on Modified Columbia Agar in the Routine Laboratory" *Journal of Clinical Microbiology* 40(9):3277-3280 (2002).

Wiese et al. "A meta-analysis of the Papanicolaou smear and wet mount for the diagnosis of vaginal trichomoniasis" *The American Journal of Medicine* 108(4):301-308 (1999).

Alderete "Identification of Immunogenic and Antibody-Binding Membrane Proteins of Pathogenic *Trichomonas vaginalis*" *Infection and Immunity* 40(1):284-291 (1983).

Alderete and Garza "Identification and Properties of *Trichomonas vaginalis* Proteins Involved in Cytadherence" *Infection and Immunity* 56(1):28-33 (1988).

Alderete and Kasmala "Monoclonal Antibody to a Major Glycoprotein Immunogen Mediates Differential Complement-Independent Lysis of *Trichomonas vaginalis*" *Infection and Immunity* 53(3):697-699 (1986).

Alderete et al. "Heterogeneity of *Trichomonas vaginalis* and Discrimination among Trichomonal Isolates and Subpopulations with Sera of Patients and Experimentally Infected Mice" *Infection and Immunity* 49(3):463-468 (1985).

Alderete et al. "Phenotypic Variation and Diversity Among *Trichomonas vaginalis* Isolates and Correlation of Phenotype with Trichomonal Virulence Determinants" *Infection and Immunity* 53(2):285-293 (1986).

Arroyo et al. "Molecular Basis of Host Epithelial Cell Recognition by *Trichomonas vaginalis*" *Molecular Microbiology* 6(7):853-862 (1992).

Arroyo et al. "Signalling of *Trichomonas vaginalis* for Amoeboid Tranformation and Adhesin Synthesis Follows Cytoadherence" *Molecular Microbiology* 7(2):299-309 (1993).

Lehker et al. "The Regulation by Iron of the Synthesis of Adhesins and Cytoadherence Levels in the Protozoan *Trichomonas vaginalis*" *J. Exp. Med.* 174:311-318 (1991).

Wasserheit "Epidemiological Synergy: Interrelationships between Human Immunodeficiency Virus Infection and Other Sexually Transmitted Diseases" *Jn. Sex. Trans. Dis.* 19:61-77 (1992).

Yap et al. "Serum Antibodies to *Trichomonas vaginalis* in Invasive Cervical Cancer Patients" *Genitouria Med.* 71:402-404 (1995).

Zhang et al. "*Trichomonas vaginalis* and Cervical Cancer: A Prospective Study in China" *Ann. Epidemiol.* 5(4):325-332 (1995).

Alderete and Garza "Soluble *Trichomonas vaginalis* Antigens in Cell-Free Culture Supernatants" *Molecular and Biochemical Parasitology* 13:147-158 (1984).

Alderete et al. "Cloning and Molecular Characterization of Two Genes Encoding Adhesion Proteins Involved in *Trichomonas vaginalis* Cytoadherence" *Molecular Microbiology* 17(1):69-83 (1995).

Alderete et al. "Monoclonal Antibody to a Major Surface Glycoprotein Immunogen Differentiates Isolates and Subpopulations of *Trichomonas vaginalis*" *Infection and Immunity* 52(1):70-75 (1986).

Alderete et al. "Phenotypes and Protein-Epitope Phenotypic Variation Among Fresh Isolates of *Trichomonas vaginalis*" *Infection and Immunity* 55(5):1037-1041 (1987).

Alderete et al. "Specific Parasitism of Purified Vaginal Epithelial Cells by *Trichomonas vaginalis*" *Infection and Immunity* 56(10):2558-2562 (1988).

Alonzo and Pepe "Using a Combination of Reference Tests to Assess the Accuracy of a New Diagnostic Test" *Statistics in Medicine* 18:2987-3003 (1999).

Arroyo et al. "Characterization of cDNAs Encoding Adhesin Proteins Involved in *Trichomonas vaginalis* Cytoadherence" *Archives of Medical Research* 26(4):361-369 (1995).

Benchimol et al. "Structure and Division of the Golgi Complex in *Trichomonas vaginalis* and *Tritrichomonas foetus*" *European Journal of Cell Biology* 80:593-607 (2001).

Cogne et al. "Detection and Characterization of Serum Antitrichomonal Antibodies in Urogential Trichomoniasis" *Jpurnal of Clinical Microbiology* 21(4): 588-592 (1985).

Cuatrecasas, Pedro "Protein Purification by Affinity Chromatography" *The Journal of Biological Chemistry* 245(12): 3059-3065 (1970).

Dalchau et al. "Monoclonal Antibody to a Human Leukocyte-Specific Membrane Glycoprotein Probably Homologous to the Leukocyte-Common (L-C) Antigen of the Rat" *Eur. J. Immunol.* 10:737-744 (1980).

Huse et al. "Generation of a Large Combinatorial Library of the Immunoglobulin Repertoire in Phage Lambda" *Science* 246: 1275-1281 (1989).

International Search Report corresponding to International application No. PCT/US03/09474 filed Mar. 27, 2003.

Köhler and Milstein "Continuous Cultures of Fused Cells Secreting Antibody of Predefined Specificity" *Nature* 256:495-497 (1975).

Lehker and Sweeney "Trichomonad Invasion of the Mucous Layer Requires Adhesins, Mucinases, and Motility" *Sex. Transm. Inf.* 75:231-238 (1999).

O'Brien et al. "Molecular Characterization of a Third Malic Enzyme-Like AP65 Adhesin Gene of *Trichomonas vaginalis*" *Microbial Pathogenesis* 20:335-349 (1996).

Van Der Schee et al. "Improved Diagnosis of *Trichomonas vaginalis* Infection by PCR Using Vaginal Swabs and Urine Specimens Compared to Diagnosis by Wet Microscopy, Culture, and Flourescent Staining" *Journal of Clinical Microbiology* 37(12):4127-4130 (1999).

Watt et al. "Rapid Assay for Immunological Detection of *Trichomonas Vaginalis*" *Journal of Clinical Microbiology* 24(4):551-555 (1986).

Wos et al. "Immunoglobulin Isotypes of Anti-*Trichomonas vaginalis* Antibodies in Patients with Vaginal Trichomoniasis" *Journal of Clinical Microbiology* 24(5):790-795 (1986).

Addis et al. "Host and Tissue Specificity of *Trichomonas vaginalis* is not Mediated by its Known Adhesion Proteins" *Infection and Immunity* 68(7):4358-60 (2000).

Alderete et al. "Only two of the *Trichomonas vaginalis* triplet AP51 adhesins are regulated by iron" *Microbial Pathogenesis* 24:1-16 (1998).

Engbring et al. "Characterization of *Trichomonas vaginalis* AP33 adhesin and cell surface interactive domains" *Microbiology* 144:3011-3018 (1998).

Engbring et al. "Three genes encode distinct AP33 proteins involved in *Trichomonas vaginalis* cytoadherence" *Molecular Microbiology* 28(2):305-313 (1998).

Lisi et al. "Monoclonal Antibody Based Enzyme Linked Immunosorbent Assay for *Trichomonas vaginalis*" *Journal of Clinical Microbiology* 26(9):1684-1686 (1998).

Correspondence from third party, dated Oct. 30, 2008 (7 pages).

METHOD AND DEVICE FOR *TRICHOMONAS* DETECTION

STATEMENT OF PRIORITY

The present application is a continuation application of, and claims priority to, U.S. application Ser. No. 10/112,410, filed Mar. 30, 2002 and issued as U.S. Pat. No. 7,291,477 on Nov. 6, 2007, which claims the benefit, under 35 U.S.C. § 119(e), of U.S. Provisional Application Ser. No. 60/302,733, filed Jul. 3, 2001 and entitled "Diagnostic Tests and Kits for *Trichomonas*," the entire contents of each of which are incorporated by reference herein.

FIELD OF THE INVENTION

The present invention relates to an immunoassay method and kit for detecting *Trichomonas* infection.

BACKGROUND OF THE INVENTION

Trichomonads are protozoan parasites that infect humans and animals. There are over 15 species of Trichomonads. *Trichomonas vaginalis* (*T. vaginalis*) is a species of Trichomonad that humans and causes the condition trichomoniasis (or "trichomonosis" or "trich") in both men and women. The parasite is sexually transmitted and is now the world's most common non-viral sexually transmitted disease (STD) agent. It is estimated that 5 to 8 million women acquire trichomoniasis annually in the United States, and up to 25% of sexually active woman are infected at any given time.

In men, trichomoniasis is estimated to account for 17% of non-chlamydial, non-gonococcal urethritis. The clinical symptoms vary tremendously among women, ranging from asymptomatic carriage to frank vaginitis; and the infection can persist indefinitely. Severe symptoms include abdominal pain with a foul-smelling discharge accompanied by irritation and discomfort similar to a vaginal yeast infection. Men tend to have more asymptomatic disease that lasts 4 months on average, but disease manifestations such as urethritis, prostatitis, balanoposthitis, and others have been documented in infected men.

In humans, infection with *Trichomonas* has severe health consequences. *Trichomonas* secretes proteinases that degrade vaginal antibodies, protective cell layers and immune response cells, thereby increasing the susceptibility of infected women to other sexually transmitted diseases. Studies have shown that women at risk for HIV have 2- to 10-fold greater risk of HIV infection if infected with *T. vaginalis*, and a male positive for both HIV and *Trichomonas* has 6 times more HIV in semen, thereby increasing the probability of infecting a partner (Wasserheit, 1992). Moreover, infection by *Trichomonas* increases the risk of acquiring cervical cancer, and can adversely affect both fertility and pregnancy (Yap et al., 1995; Zhang et al., 1995). Fortunately, if the infection by the parasite is successfully diagnosed, the patient can be treated in most cases.

The current diagnosis of trichomoniasis rests on the detection and morphologic identification of the live organism extracted from the vaginal cavity in women or the urethra in men. Identification is accomplished by microscopic examination of a saline wet mount preparation for the direct visualization of motile organisms. Although highly specific when positive, wet mounts are often negative in asymptomatic or mildly symptomatic patients and in women who have douched within the previous 24 hrs. Overall sensitivity or reliability of wet mount microscopy is 58% (Weise et al.), and can be as low as 30%. Wet mount microscopy can also be attempted from urine specimens following centrifugation to concentrate any trichomonads in the pellet, which is than resuspended and examined. Wet mount microscopy is highly inefficient when performed on urine samples, with sensitivity as low as 7% (compared to culture at 40%) (van Der Schee et al. *J. Clin Microbiol.* 1999 December: 37 (12) 4127-30). In addition, the wet mount microscopy method of detection, utilizing any of the sample types described, is subjective, tedious and time consuming, and requires a trained person Cultures of urogenital specimens may increase the number of detected cases. Unfortunately, the procedure requires several days to complete (typically 2-5 days) and must be conducted in special laboratories with trained personnel. Further, both of these methods require the parasites in the samples to be viable before they can be detected, constraining the suitability of certain sample types. For example, it has been determined that urine is not a suitable sample medium for culture-based diagnosis of *Trichomonas*, despite being more sensitive than wet mount (Mohamed et al. *Sex. Transmitted Infect.*, 2001. 77(1) 78-9). Many attempts have been made to improve the diagnosis of *Trichomonas* from urine, as well as other sample types, using PCR. Although PCR is potentially more sensitive than wet mount or culture (87% according to the above reference), there is a lack of scientific consensus on what primer sequences are *Trichomonas* specific (PCR is not an FDA approved diagnostic method). Further, the problem of false positives in both discrepant samples and contaminated clinical samples hinders the application of this technique. Highly amplified samples may provide a positive result that is not indicative of actual infection, but instead represents traces of a prior infection. In addition, PCR is a highly technical procedure with many manipulations and procedural controls, requires expensive equipment, and does not allow for point of care diagnosis; all factors mitigating against its suitability as a practical diagnostic method for *Trichomonas*.

A method for detecting *Trichomonas* infection by lysing the microorganisms in a sample and releasing their nucleic acids has been disclosed. The presence of *Trichomonas* is determined by hybridizing the released nucleic acids with probes. The method involves a large number of manipulations and the use of expensive detection equipment, and is less sensitive that wet mount microscopy.

The high frequency of *Trichomonas* infection, coupled with the likelihood of an adverse outcome for cases that are not treated expeditiously, makes clear the need for a rapid, sensitive, and accurate diagnostic test to detect *Trichomonas* infection and the ability to evaluate the effectiveness of the treatments. The diagnostic test should be suitable for use with a variety of samples suspected of containing *Trichomonas*, whether of not the sample contains live organisms, and in particular, should allow detection in a urine (for sampling men and women) and vaginal swap samples. In addition, the method should give high reliability, e.g., positive result for infected individuals.

SUMMARY OF THE INVENTION

In one aspect, the invention includes a method for detecting *Trichomonas vaginalis* infection in a human subject. In practicing the method, a body-fluid sample, such as a urine or vaginal-swab sample, is obtained from the subject and contacted with an antibody specific against a *Trichomonas* adhesin peptide, to form an antibody-adhesin peptide complex if the subject is infected with *Trichomonas*. The presence or absence of the complex is diagnostic with a reliability of at least about 80%, and typically better than 90%, where the clinical specimen is a vaginal swab, and with a reliability of higher than 40% where the clinical specimen is urine.

In a more general aspect, the invention is applicable to detect *Trichomonas* invention in mammals, e.g., cows or other domesticated animals, for example, *Tt. foetus* infection in cows, using as the antibody reagent, either an antibody against *T. vaginalis* adhesin protein, or an antibody against a homologous adhesin protein from the infecting species, e.g., *Tt. foetus*.

Exemplary adhesin proteins, for detecting *T. vaginalis* infection in humans, are *T. vaginalis* AP65, AP51, AP33, AP23 adhesin proteins, and immunologically reactive fragments thereof, particularly AP65 and AP33 adhesin protein. Likewise, an exemplary antibody is an anti-AP65 antibody, for example, the antibodies produced by the cell lines DM116 and C55. Exemplary peptides for non-human assay are homologous adhesin peptides derived from the animal-infecting *Trichomonas* species.

In one preferred assay format, the contacting step contacting includes placing the sample on a sample-application zone of a dry strip having, in an upstream to downstream direction, the sample-application region, a reaction zone containing non-immobilized labeled antibody specific against a *Trichomonas* adhesin peptide, and a detection zone containing immobilized antibody specific against *Trichomonas* adhesin peptide in the complex. In operation, (i) sample migrates in a downstream direction on said strip from the sample-application zone toward the reaction zone, (ii) adhesin peptide analyte in the sample reacts with non-immobilized antibody in the reaction zone to form a mobile labeled adhesin peptide-antibody complex, and (iii) the complex migrates toward the detection zone, (iv) said complex reacts with the immobilized antibody in the detection zone to form an immobilized labeled complex in the detection zone, and (v) non-complexed nonmobilized labeled antibody migrates downstream of the detection zone. The detecting step includes detecting the presence or absence of immobilized, labeled complex in the detection zone.

In another assay format, the sample obtained is a pap smear, and the sample is fixed (for example using ethanol or methanol). The pap smear can be a traditional pap smear or a liquid based assay, exemplified by the thin-prep pap smear produced by Cytyc. The sample is prepared in the presence of labeled antibody that detects adhesin protein that has been subjected to the denaturing conditions of the fixing process. An exemplary antibody is an AP33 antibody. The method may include treating the thin prep to remove unbound labeled antibodies.

In another aspect, the invention includes a kit for detecting *Trichomonas vaginalis* infection in a human subject. The kit includes a dry-strip capable of wicking a fluid applied thereto by capillarity within the strip, from an upstream sample-application zone, through a reaction zone, and into a downstream detection zone. The reaction zone contains a non-immobilized labeled antibody specific against a *Trichomonas* adhesin peptide, effective to form therewith, a mobile adhesin-protein-antibody complex, and the detection zone contains immobilized antibody specific against *Trichomonas* adhesin peptide in the complex. After application of a body-fluid sample to the sample-application zone, (i) sample migrates in a downstream direction on the strip toward the reaction zone, (ii) adhesin peptide analyte in the sample reacts with non-immobilized capture antibody in the reaction zone to form a mobile labeled adhesin peptide-antibody complex, (iii) the complex migrates toward the detection zone, (iv) the complex reacts with the immobilized antibody in the detection zone to form an immobilized labeled complex in the detection zone, and (v) non-complexed nonmobilized labeled antibody migrates downstream of the detection zone. The presence or absence of *Trichomonas* infection in the subject is determined by the presence or absence of detectable label in the detection zone.

An exemplary non-immobilized antibody in the kit is immunospecific against an AP65, AP51, AP33, AP23 adhesin protein, and immunologically reactive fragments thereof, of which AP65 is preferred. An exemplary antibody in the kit is the antibody produced by DM116 cell line.

In still another aspect, a method for detecting *Trichomonas* infection in a human subject comprises the steps of obtaining a body-fluid sample from the subject, such as saliva or blood, and contacting the sample with a *Trichomonas* adhesin peptide, to form an antibody-adhesin peptide complex if the subject is infected with *Trichomonas*. The presence of absence of the complex is detected to establish the presence or absence, respectively, of *Trichomonas* infection in the subject.

Exemplary adhesin peptides are AP65, AP51, AP33, AP23 adhesin proteins, and immunologically reactive fragments thereof.

In one assay format, the sample is placed on a sample-application zone of a dry strip having, in an upstream to downstream direction, the sample-application region, a reaction zone containing labeled, non-immobilized *Trichomonas* adhesin peptide, and effective to react with anti-*Trichomonas* antibody present in a *Trichomonas*-infect individual to form a mobile antibody-adhesin peptide complex, and a detection zone containing immobilized capture antibody specific against human antibody. After application of the sample, (i) the sample migrates in a downstream direction on the strip toward the reaction zone, (ii) anti-*Trichomonas* antibody analyte in the sample reacts with labeled, non-immobilized adhesin peptide in the reaction zone to form a mobile labeled adhesin peptide-antibody complex, and (iii) the complex migrates toward the detection zone, (iv) the complex reacts with the immobilized antibody in the detection zone to form an immobilized labeled complex in the detection zone, and (v) non-complexed nonmobilized labeled adhesin migrates downstream of the detection zone. An exemplary immobilized antibody in the kit is the antibody produced by the C55 cell line. The presence or absence of immobilized labeled complex in the detection zone is determined by the presence of absence of labeled complex in the detection zone.

These and other objects and features of the invention will be more fully understood when the following detailed description of the invention is read in conjunction with the accompanying drawings.

DETAILED DESCRIPTION OF THE INVENTION

1. Definitions

Figure 1:
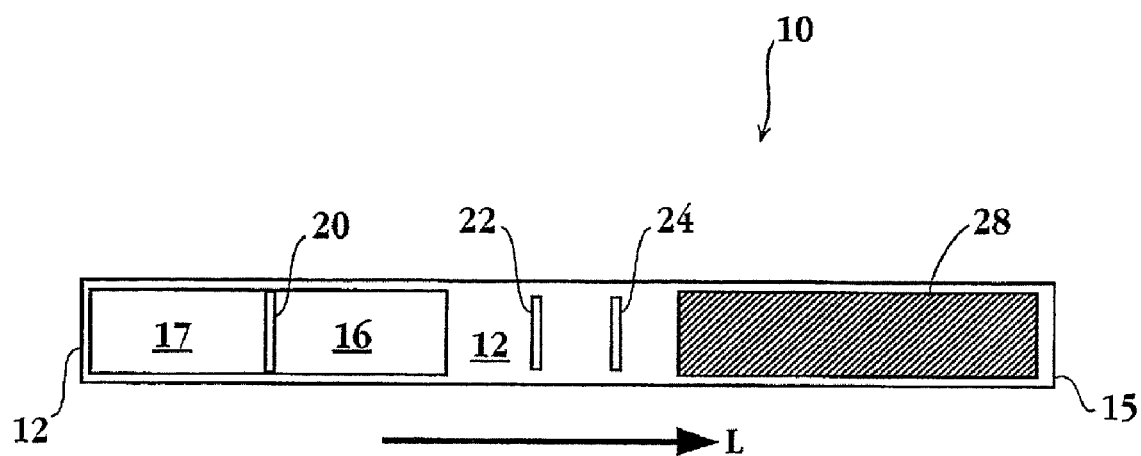
FIG. 1 shows the top plane view of a test strip in a *Trichomonas*-assay kit in accordance with the invention.

The terms below have the following meanings, unless indicated otherwise in the specification.

The term "*Trichomonas*", as used herein, includes, but is not limited to a protozoan parasite of the Order Trichomonadida, Genera *Ditrichomonas, Trichomonas, Tritrichomonas*, and *Pentatrichomonas*, comprising multiple species that infects both humans and animals. "*Trichomonas*" refers to any *Trichomonas* species, e.g., *Tritrichomonas foetus* (also known as *Trichomonas foetus, Tt. fetus*), *Tt. enteris*, and *T. paviovi* which infects cattle, *Tt. suis, Tt. rotunda*, and *T. buttreyi* which infects swine, *Dt. ovis* which infects sheep, *Tt. equi*, and *T. equibuccalis* which infects horses, *T. anatis, Tt. eberthi, T. gallinae*, and *T. gallinarum*, which infect birds, *Tt. caviae, Tt. muris, Tt. wenoni, Tt. minuta*, and *T. microti* which infect rodents, *T. canistomae* and *T. felistoniae*, which infect dogs and cats, and *T. tenax, T. vaginalis, Pt. Hominis*, and *T. macacovaginae*, which infect primates (including humans) in biological samples. In the case of the human disease, "*Trichomonas*" refers to, but is not limited to, the species *Trichomonas vaginalis (T. vaginalis)*. "*Trichomonas vaginalis*" refers to any strain of *T. vaginalis* capable of infecting humans.

The term "antibody," as used herein, includes, but is not limited to a polypeptide substantially encoded by an immunoglobulin gene or immunoglobulin genes, or fragments thereof, which specifically bind and recognize an analyte (antigen or antibody). "Antibody" also includes, but is not limited to, a polypeptide substantially encoded by an immunoglobulin gene or immunoglobulin genes, or fragments thereof, which specifically bind and recognize the antigen-specific binding region (idiotype) of antibodies produced by the host in response to exposure to trichomonas antigen(s). Examples include polyclonal, monoclonal, chimeric, humanized, and single chain antibodies, and the like. Fragments of immunoglobulins include Fab fragments and fragments produced by an expression library, including phage display. See, e.g., Paul, FUNDAMENTAL IMMUNOLOGY, 3.sup.rd Ed., 1993, Raven Press, New York, for antibody structure and terminology.

The term "epitope" means an antigenic determinant capable of specific binding to an antibody. Epitopes usually consist of surface groupings of molecules such as amino acids or sugar side chains and usually have specific three-dimensional structural characteristics, as well as specific charge characteristics.

The terms "specifically binds to" and "specifically immunoreactive with" refer to a binding reaction that is determinative of the presence of the target analyte in the presence of a heterogeneous population of proteins and other biologics. Thus, under designated assay conditions, the specified binding moieties bind preferentially to a particular target analyte and do not bind in a significant amount to other components present in a test sample. Specific binding to a target analyte under such conditions may require a binding moiety that is selected for its specificity for a particular target analyte. A variety of immunoassay formats may be used to select antibodies specifically immunoreactive with a particular antigen. For example, solid-phase ELISA immunoassays are routinely used to select monoclonal antibodies specifically immunoreactive with an analyte. See Harlow and Lane, ANTIBODIES: A LABORATORY MANUAL, Cold Springs Harbor Publications, New York, (1988) for a description of immunoassay formats and conditions that can be used to determine specific immunoreactivity. Typically a specific or selective reaction will be at least twice background signal to noise and more typically more than 10 to 100 times greater than background.

A "protein" refers to a biopolymer composed of amino acid or amino acid analog subunits, typically some or all of the 20 common L-amino acids found in biological proteins, Although "protein" commonly refers to a relatively large polypeptide, e.g., containing 100 or more amino acids, and "peptide" to smaller polypeptides, the terms are used interchangeably herein. That is, the term protein may refer to a larger polypeptide, as well as to a smaller peptide, and vice versa.

An "immunologically reactive fragment" of a protein refers to a portion of the protein that is immunologically reactive with a binding partner, e.g., antibody, which is immunologically reactive with the protein itself.

"Specificity", as it relates to the assay method of the invention, refers to the ability of the assay to specifically detect *Trichomonas* infection.

"Reliability", as it relates to the assay method of the invention, refers to the percentage of a population that is detected as a true positive. For example, at least 80% reliability means that the assay will detect *Trichomonas* infection in at least 80% of the subjects tested who are in fact *Trichomonas* infected, as determined, for example, by a confirmatory test such as culture or PCR. The term is also used interchangably with "sensitivity."

II. The Assay of the Invention

The present invention is based on the discovery herein that *Trichomonas* infection, particularly *T. vaginalis* infection in humans, can be easily detected with high sensitivity, by forming an immune complex between a *Trichomonas* adhesin protein, or immunoreactive fragment thereof, and an antibody that is immunospecific against this protein, and detecting the complex. In one general embodiment, *Trichomonas* infection is detected by the presence of adhesin protein or immunological fragments thereof in a body sample, e.g., urine sample or vaginal swab. In this embodiment, the assay reagent is a labeled anti-adhesin antibody capable of forming a detectable complex with the adhesin protein present in the sample. An important advantage of this test is that such adhesin proteins have been found to be present in detectable amounts in the vaginal swabs, i.e. vaginal secretion, scrapings or swabs from the vaginal tract or cervix. or cervical canal, or pap smear, in virtually all *Trichomonas*-infected women who have been tested for *Trichomonas* infection by the present assay. Similarly, adhesin protein has been found in detectable amounts in urine in *Trichomonas*-positive men and women who have been tested by the assay of the invention. Thus, the assay is highly sensitive, and can be carried out readily in men, with a urine sample, as well as women, with either a urine or vaginal or cervical swab sample.

In another general embodiment, the *Trichomonas* infection is detected by the presence of a body-sample antibody that is immunoreactive with a labeled *Trichomonas* adhesin protein assay reagent. In this embodiment, the labeled assay reagent is a labeled *Trichomonas* adhesin protein that is capable of forming a detectable complex with an anti-adhesin antibody present in an infected individual.

The assay of the present invention is based on immunological binding reactions. For a review of the general procedures of immuno-assays, see BASIC AND CLINICAL IMMUNOLOGY, 7.sup.th Edition, D. Stites and A. Terr, ed., 1991, which is hereby incorporated by reference. In one embodiment of the invention, the assay detects the presence of a *Trichomonas* immunogen. In another embodiment of the invention, the assay detects host generated anti-*Trichomonas* antibodies. The presence of either the *Trichomonas* immunogen or host generated anti-*Trichomonas* antibodies in a biological sample are indicative of the occurrence of *Trichomonas* infection.

The assay of the invention is highly specific and sensitive. As noted above, It has been demonstrated that the assay of the invention specific for *T. vaginalis* has a greater than about 80% sensitivity, and that 21% of wet mount-negative patients (28/131) are test-positive with T vaginalis (using culture as confirmatory, or resolving, test). This increased level of sensitivity allows for the identification of an additional 37% of *Trichomonas* infected patients (103/75). Overall specificity of the assay of the present invention is about 98%.

In practicing the method, one first obtains a body-fluid sample from the test subject. Where, as in the preferred embodiment, the test subject is a human, a suitable body fluid sample is a vaginal swab, i.e., vaginal secretion, scrapings or swabs from the vaginal tract or cervix, or cervical canal, or pap smear, in women, or a urine sample in women or men. Other suitable body fluid, particularly for detecting anti-*Trichomonas* antibody, includes serum, blood, and saliva. Where the test subject is a veterinary or domestic animal, suitable body fluids such as urine and mucosal swabs are selected.

Alternatively, the sample may consist of cells from the patient for example, or from any site of infection including but not limited to the cervical canal, uterus, fallopian tubes, testes, anus, throat, lungs, skin, eyes, gastro-intestinal tract, or body cavity. These samples can be used fresh, or stored (frozen, dried, refrigerated, as appropriate) for later use. The samples can be used in their native form (urine), or processed, extracted, solubilized, or manipulated. The *Trichomonas* in these samples can be either viable or dead, whole cell or disrupted, processed or unprocessed.

The development of immunoassays for the detection of *Trichomonas* has been largely unsuccessful due to the lack of stable, species dependent antigen. The success of the present invention relies in part on the stability of adhesin protein in *Trichomonas*. *Trichomonas* has exhibited dramatic antigenic heterogeneity (Alderete et al., 1985b; 1986a, 1987a). In order to establish and maintain infection, the parasite is capable of withstanding the hostile environment of the urogenital tract and evading immune surveillance mechanisms, such as resisting lytic antibodies and complement of the host. The parasite has developed the ability to undergo phenotypic shifting (Alderete et al., 1986; Alderete et al., 1985), a strategy used by many parasites to evade detection. It has been observed that isolates taken from the same patient at two different times can exhibit different phenotypes (Alderete et al., 1987). It has also been observed that the parasite undergoes phenotyic shifting in response to its environment. For example, the in vivo environment apparently favors or selects for *T. vaginalis* organisms lacking the expression of a particular surface immunogen (P270), but upon in vitro cultivation, the parasites revert to the opposite phenotype producing P270. In another example, the adhesin protein AP65 is expressed at low levels in typical culture environments, but is expressed at significantly higher levels in the host, or an in vivo-like environment. Thus, antibodies raised against organisms cultured under in vitro conditions may not be effective for binding to *Trichomonas* contained in vivo samples. Based on its level of expression by *Trichomonas* grown in a typical culture environment, the adhesin AP65 protein would not be readily appreciated as a potential analyte for use in a diagnostic assay. Furthermore, the parasite is proteolytic, that is, it is capable of secreting proteases that degrade surface antigens and antibodies. As a result of the above defensive mechanisms, there is no known stable immunogen in the environment for the development of anti-*Trichomonas* antibodies.

*Trichomonas* adhesin proteins are typically surface expressed proteins, and have been associated with cytoadherence of the parasite to the epithelial cells lining the urogenital tract of the host animal (Alderete and Garza, 1988, Arroyo et al., 1992; Lehker et al., 1991). In addition, adhesins are functionally active enzymes.

Adhesin proteins are not obvious candidates for diagnostic use by persons practiced in the art due their being metabolic enzymes and the fact that they are not expressed in typical culture environments. Metabolic enzymes share fundamental roles in all organisms and are therefore highly conserved and share homology with ubiquitous host proteins (such as other metabolic enzymes). Antigens that share homology with commonly found proteins are generally unsuited for antibody production and use in diagnostic tests. They are typically not immuno-reactive, or have a very low likelihood of elicit strong immune responses. Thus, such antigens are less likely to induce sufficient infection-response antibodies for detection, nor generate suitable poly- and monoclonal antibodies for detection of the antigen itself. It has also been reported that the adhesins appear to be immunorecessive, as evidenced by the difficulty of generating high-titered antiserum and monoclonal antibodies (mAbs) in experimental animals (Alderete and Garza, 1988; Arroyo et al., 1992, 1993; Lehker et al., 1991). Furthermore, antibodies directed to such antigens are likely to suffer from low specificity, due to reactions with similar proteins from the host and other co-pathogens. Indeed, the similarity (mimicry) of adhesins to host proteins may underlie the pathogens' ability to evade detection and immune attack. The inventors determined that certain adhesin proteins are highly expressed in animal hosts and are immunoreactive under special in vivo like cultured environments; the adhesin also expressed in sufficient quantity, which allows the raising of antibodies. Thus, the selection of the adhesin proteins represents a novel strategy in antigen selection for immunologically-based diagnostic assays.

The adhesin proteins and their coding sequences for the human parasite *T. vaginalis* have been disclosed in U.S. Pat. No. 5,922,563 and the disclosure of which is incorporated herein by reference. Four families of adhesin proteins (AP65, APS1, AP33, and AP23) are identified as the adhesins that specifically mediate attachment to receptors of the vaginal epithelial cells. The four T. vaginalis adhesin families are grouped based on their relative molecular weights ($M_r$), AP65 (65-kDa), AP51 (51-kDa), AP33 (33-kDa), and AP23 (23-kDa). At least three of the adhesin families include members having distinctive nucleic acid references that may be closely related. Therefore, each respective adhesin is a member of a multigene family, and, as used herein, the terms AP65, AP51, AP33, and AP23 will designate all members of the corresponding $M_r$ *T. vaginalis* adhesin protein families. In addition, the adhesins are present in the genome of *T. vaginalis* in multiple copies.

In one embodiment of the invention, the AP65 adhesin protein family is selected as the immunogen for the diagnostic assay. While AP65 is preferred, other stable, adhesin proteins may be selected as the immunogen for the diagnostic assay. The gene for the AP65 protein is approximately 1.8 kb in length. The family of AP65 adhesin proteins includes six known members, three of which have (AP65-1, AP65-2, and AP65-3), have been described in detail, e.g., in U.S. Pat. No. 5,922,563 to Alderete, which patent is incorporated herein by reference. Each of the members is encoded by a distinct AP65 gene. The AP65-1 and AP65-2 N-terminal sequences are very similar, with 9 of 12 amino acids being identical. The hydropathy plots (Kyte and Doolittle 1982) of AP65-1, AP65-2 and Ap65-3 are very similar with only a few differences. The AP65 adhesin proteins are unique to *T. vaginalis*. It has been demonstrated using a ligand assay performed simultaneously with a cross-hybridization study using cDNA inserts as probes to *T. vaginalis, T. suis* (the porcine trichomonad) and *Tt. foetus* (the bovine trichomonad), that the serum produced from *T. vaginalis* adhesins exhibits no cross-reactivity with the other species.

A. Assay Format

The assays of the invention can be either direct or competitive. In a competitive binding assays, the target analyte, e.g., a *T. vaginalis* adhesin protein, competes with a labeled analyte analog for specific binding sites on a preferably immobilized binding agent, e.g., antibodies that specifically bind the adhesin protein, bound to a suitable solid surface, e.g., nitrocellulose, nylon, PVC or polystyrene surfaces. The concentration of labeled analyte bound to the capture reagent is inversely proportional to the amount of free analyte present in the sample, which can be qualitatively detected in solution or bound form, or can be quantitated, e.g., by spectrophotometric determination of labeled adhesin protein in solution.

Direct assays are typically sandwich assays, in which the target analyte, e.g., a T vaginalis adhesin protein, binds both to a labeled binding agent, e.g., labeled antibody, and an immobilized capture antibody, forming an immobilized labeled sandwich complex that can be detected. The exact format of the assay generally depends on the sensitivity or specificity expected for the assay. In some assays, particularly for those assays employing labile reagents, a control reagent may be added to confirm the effectiveness of either the labeled or the capture reagent.

In another direct-binding assay format, used particularly for pap-smear analysis, a cervical swab sample from a female subject is treated to remove interfering substances, and deposited on a solid where the swab components, e.g., *T. vaginalis* adhesin proteins, are immobilized, e.g., by binding to a treated glass slide surface. A labeled binding agent, e.g., a fluorescence labeled anti-adhesin antibody is then applied to the slide, allowed to bind to immunospecific targets, followed by washing to remove unbound antibody. The presence of absence of analyte in the swab sample can then be determined by fluorescence microscopic examination of the slide. U.S. Pat. Nos. 6,174,742 and 5,741,662, as examples, describe methods for collecting and treating vaginal swab material, and for detecting stained material. One suitable format for a pap-smear test is the Thin-Prep® pap test supplied by Cytyc.

One preferred embodiment of a direct-assay format, is the dry-strip assay kit, which is detailed in Section III below. In this assay format, a porous or fibrous test strip that allows for capillary flow therethrough includes, in an upstream-to-downstream direction, a sample-application zone, a reaction zone, and a detection zone. The sample-application zone may be simply an area on the strip at which sample is to be added. The reaction zone contains a non-immobilized labeled reagent capable of binding to sample analyte, e.g., an adhesin protein, to form a labeled mobile complex, that is, a complex capable of migrating through the test strip, typically by capillary flow, in a downstream direction toward the detection zone. Where the analyte is an adhesin protein, the labeled reagent is typically a labeled anti-adhesin antibody, as detailed below. Where the analyte is an anti-*Trichomonas* antibody, the labeled reagent is a labeled adhesin protein. Typically, the reagent is added to the strip in soluble form, and allowed to dry, such that upon wetting, with application of sample to the strip, the dried reagent can enter the soluble phase and migrate through the strip medium. Details are given below, including Example 3.

The detection zone contains an immobilized capture reagent capable of binding to the analyte moiety of the mobile complex, to immobilize the labeled complex in this zone, while labeled, but non-complex reagent passes through the zone with the moving sample-fluid medium. The immobilized binding reagent may be covalently bound to the strip matrix or tightly bound by non-covalent linkage, e.g., electrostatic or dispersion forces. In any event, the immobilization is sufficient to allow the binding reagent to capture and immobilize labeled complex, as sample fluid migrates through the detection zone. Where the analyte is an adhesin protein, the immobilized binding reagent is preferably an anti-adhesin antibody capable of binding specifically to an adhesin epitope that is accessible in the analyte in complex form. That is, the labeled antibody and immobilized capture antibody preferably recognize separate and distinct epitopes in the adhesin proteins. Where the analyte is a human anti-*Trichomonas* antibody, the binding agent is preferably a non-human anti-human antibody having general immunoreactivity with human antibodies.

The strip may further include a second capture zone at which non-complexed labeled reagent may be captures, to serve as a control to confirm that labeled reagent is being released from the reaction zone for movement through the strip, and that the labeled reagent is being captured by immobilized capture agents. Where the labeled reagent is a labeled anti-adhesin antibody, the control capture agent is preferably an antibody that is immunoreactive with the labeled antibody. Thus, for example, if the labeled antibody is a mouse monoclonal antibody, the control capture reagent could be a rabbit anti-mouse antibody.

As seen, by using different combinations of labeled reagent and capture reagents, the assay of the invention is adaptable for the detection of either immunogen of *Trichomonas* or host generated anti-*Trichomonas* antibodies; the presence of which in a biological sample of an animal is indicative of *Trichomonas* infection. For example, an assay specific for the detection of an immunogen of *Trichomonas*, e.g., the AP 65 adhesin protein of *T. vaginalis*, the binding moiety in the labeled and capture reagents are antibodies raised against AP65 of *T. vaginalis*, and antibodies or antigens which are specific for the constant (non-epitope) region of the labeled reagent are used as control reagent. An assay specific for the detection of host generated antibodies, e.g., anti-AP65 antibodies, the binding moiety in the labeled and capture reagents are AP65 adhesin proteins. The adhesin proteins can be either native, chimeric, fragments or a recombinant form of the AP65 adhesin protein.

Similarly, the assay of the invention is adaptable, by using different labeled and capture reagents specific to different variants of *Trichomonas*, to detect different variants of *Trichomonas*. For example, when antibodies specific for *T. vaginalis* that are infected with dsRNA virus are used, the assay may differentiate between virus infected *T. vaginalis* and virus-minus *T. vaginalis* isolates. In another example, the diagnostic assay may use antibodies to detect the presence or absence of analytes that confer, or otherwise indicate, drug resistance or drug susceptibility of the Trichomonad. Such an assay could, for example, guide therapy decisions in regard to the particular dose or drug type suited to treat a particular infection.

There are a wide variety of labels that may be used with a binding moiety (antibody or antigen) to form a labeled reagent. The choice of the label depends on the sensitivity required, ease of conjugation with the binding moiety, stability requirements, available instrumentation, and disposal provisions. Labels of the present invention may be soluble or particulate, metallic, organic, or inorganic, and may include spectral labels such as green fluorescent protein, fluorescent dyes (e.g., fluorescein and its derivatives, rhodamine and its derivatives, biotin, avidin, and streptavidin), chemiluminescent compounds (e.g., luciferin and luminol); and enzymes (e.g., horseradish peroxidase, alkaline phosphatase, etc.), spectral colorimetric labels such as colloidal gold, or carbon particles, or colored glass or plastic (e.g. polystyrene, polypropylene, latex, etc.) beads.

The label can be coupled directly or indirectly to a component of the binding moiety according to methods well known in the art, such as those described in U.S. Pat. Nos. 4,863,875 and 4,373,932, each of which is incorporated herein by reference. Non-radioactive labels are often attached by indirect means. Generally, a ligand molecule (e.g., biotin) is covalently bound to the binding moiety. The ligand then binds to an anti-ligand (e.g., streptavidin) molecule which is either inherently detectable or is covalently bound to a signal system such as a detectable enzyme, a fluorescent compound, or a chemiluminescent compound. The label may be attached to the binding moiety by a chemical linker. Linker domains are typically polypeptide sequences, such as poly-gly sequences of between about 5 and 200 amino acids. Preferred linkers are often flexible amino acid sub-sequences. Such flexible linkers are known to persons skilled in the art. For example, poly(ethylene glycol) is available commercially (Shearwater Polymers, Inc. Huntsville, Ala.). The detection moiety can also be conjugated directly to the signal-generating compound, e.g., by conjunction with an enzyme or fluorophore.

The presence of a label can be detected by inspection, or a detector that monitors a particular probe or probe combination. Typical detectors include spectrophotometers, phototubes and photodiodes, microscopes, scintillation counters, cameras, film and the like, as well as combinations thereof. Examples of suitable detectors are widely available from a variety of commercial sources known to persons skilled in the art.

For purposes of the present invention, preferred labels are non-radioactive and are readily detected without the use of sophisticated instrumentation. Preferably, the labels will yield a visible signal that is immediately discernable upon visual inspection, or by fluorescence detection. Preferred labels include those that may be observed as: 1) chemiluminescence (using horseradish peroxidase and/or alkaline phosphatase with substrates that produce photons as breakdown products); 2) color change (colloidal gold, which produces a colored precipitate with the immuno-reactive event), and 3) fluorescence (using, e.g., fluorescein, and other fluorescent tags). In one preferred embodiment of the invention, colloidal gold is used as the label and the label is directly conjugated to the binding moiety (the antibody or antigen). When gold is used as the label, the reaction of labeled reagent-analyte complex with the capture reagent results in the appearance of a red colored deposit. As will be appreciated by one of skill in the art, the color that appears upon the reaction of the complex with the capture reagent immobilized at the capturing zone will depend on the label used.

In a preferred assay format of the invention, the capture and control capture reagents are immobilized on a solid substrate. There are a variety of solid supports known to the art that are suitable for use with the present invention. For instance, the solid support may be beads, membranes (e.g., nitrocellulose), microtiter wells (e.g., PVC or polystyrene), strings, plastic, strips, or any surface onto which antibodies may be deposited or immobilized. In addition, a wide variety of organic and inorganic polymers, both natural and synthetic, may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that may be employed include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers that form several aqueous phases, such as dextrans and polyalkylene glycols or surfactants, such as phospholipids or long chain (12-24 carbon atoms) alkyl ammonium salts and the like are also suitable.

The manner of linking a wide variety of compounds to various surfaces is well known and is amply illustrated in the literature. See, for example, IMMOBILIZED ENZYMES, Ichiro Chibata, Halsted Press, New York, 1978, and Cuatrecasas, 1970, the disclosures of which are incorporated herein by reference. The capturing and control reagents may be covalently bound or non-covalently attached through nonspecific bonding. If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. In addition to covalent bonding, various methods for noncovalently binding an assay component can be used. Noncovalent binding is typically nonspecific absorption of a compound to the surface. Typically, the surface is blocked with a second compound to prevent non-specific binding of labeled assay components.

In a preferred embodiment of the invention, the capture and control reagents are nonspecifically absorbed on a nitrocellulose membrane and blocked by a blocking buffer (0.5% BSA; 4% sucrose in PBS) as described in Example 3.

In one preferred embodiment, the assay detects a *Trichomonas* specific immunogen, e.g., the AP65 adhesin proteins of *T. vaginalis*. The binding moieties of the labeled and capture reagents are antibodies raised against or directed substantially against epitopes of the immunogen. The assay further includes a control reagent that can be either an internal or an external control. An internal control may consist of an anti-antibody potentially obtained from a species that is different from the species used to raise the antibodies of the labeled reagent and the capture reagent, that is, if the labeled reagent and the capture reagent were obtained from rabbit, then the antibody deposited at the control region may be goat anti-mouse IgG, sheep anti-mouse IgG, pig anti-mouse IgG, and the like. The production of such antibodies is discussed below. An external control may consist of antigens derived from *Trichomonas*, either from cellular purification, crude extracts, or recombinant proteins to which the labeled reagent and the capture reagent will bind.

The antibodies can be either a monoclonal antibody or a polyclonal antibody, but is preferably a monoclonal antibody. Single chain antibodies and fragments of antibodies are also useful as binding moieties. Thus, the term "antibody," as used herein, also includes single chain antibodies and antibody fragments either produced by the modification of whole antibodies or those synthesized de novo using recombinant DNA methodologies.

Antibodies used in the assay of the invention may be obtained by conventional antibody development techniques. See, e.g., Harlow and Lane, eds., ANTIBODIES; A LABORATORY MANUAL, Coldspring Harbor Laboratory, Coldspring, N.Y. Suitable inoculant for preparing the antibodies includes but not limited to the native protein, a recombinant protein, a crude membrane preparation or a crude preparation of the parasite. Suitable antibodies should be immunoreactive under aqueous and ionic and non-ionic detergent buffer conditions.

Polyclonal antibodies may be prepared, e.g., as described in Harboe and Ingild, Scand. J. Immun. 2 (Suppl. 1), p. 161-164, (1973). More specifically, when polyclonal antibodies can be obtained by inoculating any of various host animals, including but not limited to rabbits, mice, rats, sheep, goats and the like, with the above described inoculant in a suitable adjuvant, such as Freund's incomplete or complete adjuvant. The inoculation may be followed by one or more booster injections at suitable intervals (e.g., one or two weeks to a month). The animals are bled regularly, for instance at weekly intervals, and the antibody is isolated from the serum.

Preferably, the monoclonal antibody is produced by use of a hybridoma cell line (e.g. as described by Kohler and Milstein, Nature 256, 1975, p. 495, or U.S. Pat. No. 4,707,442 to Alderete). Several myeloma cell lines may be used for the production of fused cell hybrids, including P3/X63-Ag 8, P3/NSI/1-Ag 4-1, Sp2/10-Ag14 and S194/5.XXO.BUT.1. In a typical fusion procedure, spleen lymphocytes from an animal immunized against a chosen antigen are fused with myeloma cells. The resulting hybridomas are then dispersed in a series of separate culture tubes or microtiter plate wells to screen for cultures producing a desired antibody. Positive cultures are further diluted to obtain colonies arising from a single cell (clones). The clones are again screened for production of the desired antibody. Hybridoma cells used to make monoclonal antibody may be grown in vitro or in the body cavity of an animal. Monoclonal antibodies may be isolated and purified from supernatants of cultured hybridoma cells or from ascites using conventional procedures such as centrifugal filtration, precipitation, chromatography or a combination thereof.

In one preferred embodiment of the invention, the binding antibodies are raised against the adhesin protein AP65 of *T. vaginalis* and are produced by the DM116 and C55 cell lines. These and other anti-adhesin Mabs are deposited in the Hybridoma Depository at the University of Texas Health Science Center, San Antonio, Tex. Such antibodies may be made with high probability and predictability, using either of the two general methods that have been disclosed in the above-cited references, which are incorporated herein by reference.

In a first general method, animals, e.g., mice are injected with whole cells or membrane proteins from *T. vaginalis*. (see, for example, Alderete, 1986). Antibody producing cells from the mice are immortalized and the Mabs produced by the immortalized cells are screened from reactivity with *T. vaginalis*, e.g., in culture. The Mabs are then further screened for reactivity against one or more adhesin proteins. To identify two Mabs that interact with different epitopes of the same adhesin protein, the protein can be divided into separate overlapping fragments, e.g., of 10-25 amino acid residues, and these fragments further screened for immunoreactivity to the two or more Mabs identified as above that are immunoreactive with the different individual adhesin fragments. Alternatively, standard competitive binding studies can be employed to test pairs of Mabs that bind to different epitopes of the same adhesin protein.

In another general method, adhesin proteins or protein fragments, prepared for example, by recombinant expression of *T. vaginalis* adhesin coding sequences, as disclosed, for example, in above-cited U.S. Pat. No. 5,922,563. The isolated adhesin protein(s) or protein fragment(s) are then used directly as an immunogen, e.g., in mice, for producing hybridoma cell lines. Mabs produced by the cell lines are then screened for antibodies immunoreactive against adhesin protein. One of the methods disclosed above may then be employed to identify two or more Mabs that are immunoreactive with different epitopes of the adhesin protein.

Adhesin antibodies have been made on multiple occasions using a variety of different approaches. For example, hybridoma cell lines secreting anti-AP65 antibodies have been generated from inoculations of mice against either whole *Trichomonas* organisms, *Trichomonas* membrane preparations, purified native AP65, recombinant AP65 or formaldehyde and p-gluteraldehyde-fixed whole *Trichomonas* organisms. Adjuvants used included Freund's adjuvant, acrylamide (in the case of gel purified protein) and the non-AP65 moiety of chimeric proteins fused to AP65. Typical yields of cell lines producing immunoreactive antibodies are 5-10% of the total cell lines generated from the hybridoma fusions, a rate consistent with typical rates for the generation of other non-adhesin antibody cell lines.

The binding moiety of the labeled and capture reagents are *Trichomonas* adhesin proteins, e.g., *T. vaginalis* adhesin proteins, such as *T. vaginalis*, AP65, AP51, AP33, AP23 adhesin proteins, and immunologically reactive fragments thereof, particularly AP65 adhesin protein or an immunological fragment thereof. For use in the assay of the invention, the *Trichomonas* adhesin protein can be native, chemically synthesized or recombinantly produced, whole molecule or fragments. In one embodiment, the adhesin protein is prepared by recombinant means. The method of preparing recombinant immunogens containing at least one immunoreactive epitope are also known to those skilled in the art; and has been disclosed in U.S. Pat. Nos. 5,876,985 and 5,922,563; the disclosures of which are incorporated herein by reference. Briefly, the recombinant immunogen can be prepared using an expression vector containing a gene or genes encoding the antigen. The encoding genes may be selected from a cDNA expression library of the target Trichomonad by screening the library with a polyclonal antibody that is raised against a crude preparation of the antigen of interest. The cDNA inserts from those expression plasmids that express the antigen of interest are then subcloned and sequenced. The antigen encoding inserts that encode the different members of a family of immunogens, or of several unrelated immunogens, are pooled, and cloned into an expression vector and used to transform *E. coli* or other suitable host cells. Exemplary coding sequences for various *T. vaginalis* adhesin protein are given in the above-cited U.S. patents. In one embodiment of the invention, where the immunogen is the adhesin protein family AP65 of *T. vaginalis*, the recombinant antigen is expressed from a cassette of six nearly identical AP65 adhesin genes having a conserved epitope. The resultant recombinant antigen is highly conserved and is stable for the development of antibodies. However, it is understood that different numbers of genes and gene fragments may be included in the expression cassette to produce a recombinant antigen mixture, and the selection of appropriate genes and gene fragments is within the knowledge of those of skill in the art.

To select immunological fragments having the desired immunoreactivity of the parent or native adhesin protein, the protein can be fragmented, e.g., by proteolytic digest, and fragments tested for binding to antibodies against the native protein. Limited N-terminal or C-terminal amino acid analysis of the bound fragments can be used to identify the binding fragments of interest. Alternatively, in a recombinant expression setting, the adhesin coding sequence can be fragmented by conventional means to form fragments capable of coding adhesin fragments of between about 25-300 amino acids in length. The fragment so encoded can be analyzed conventionally in a standard expression system, e.g., gt10 or gt11 expression system, by selection against a labeled anti-adhesin antibody.

III. Dry Strip Assay Kit

The kit of the invention, referred to above as a dry-strip lateral flow assay kit, provides a "one step" lateral flow assay for the detection of a *Trichomonas* analyte (adhesin proteins or anti-*Trichomonas* antibodies) present in a biological sample. As described above, the kit generally includes a matrix composed of a material that allows for capillary flow of the sample solution along a flow path. The matrix defines a sample-application zone, a reaction zone, a detection zone, and optionally a control capture zone.

The matrix of the assay device will typically be a porous material capable of non-bibulous lateral flow. By "non-bibulous lateral flow", it is meant liquid flow in which all of the dissolved or dispersed components of the liquid are carried at substantially equal rates and with relatively unimpaired flow laterally through the membrane, as opposed to preferential retention of one or more components as would occur, e.g., in materials capable of adsorbing or imbibing one or more components.

A typical non-bibulous matrix material is a glass fiber filter paper. Other non-bibulous membranes such as polysulfone microporous membrane, nitrocellulose, cellulose acetate membrane, polyvinyl chloride, polyvinyl acetate, copolymers of vinyl acetate and vinyl chloride, polyamide, polycarbonate, nylon, orlon, polyester, polyester, polystyrene, and the like, or blends can also be used. The selection of matrix material with the desirable material properties and flow rate is generally within the knowledge of those skilled in the art.

The size and shape of the matrix are not critical and may vary. Generally, the matrix is rectangular and the flow path is axial. The porous matrix is generally backed by a generally water impervious solid support. The matrix may also be contained within, or partially within, a housing or container, typically made from plastic or similar water resistant material.

An absorbent zone is generally included in the devices of the present invention. The absorbing zone is located downstream from the capture zone. The absorbent zone is a means for removing excess sample and unbound label from the matrix of the device, in order to maintain the desired capillary flow along the flow path. Generally, the absorbing zone includes an absorbent material such as filter paper, a glass fiber filter, or the like.

A fluid sample, typically an extracted endocervical or vaginal swab, urine, or serum or saliva is applied to the matrix at the sample receiving zone. As the prepared sample flows tlu-ough the detection zone, the labeled reagent binds the target analyte forming a labeled reagent-analyte complex, if the analyte is present in the sample. As the sample flows into the capture zone, the labeled target analytes will be bound by the immobilized immunoglobulins thereby retaining the label in the capturing zone. As the sample flows into the control zone, excess labeled reagent carried in with the sample fluid, will be bound by the control reagent thereby retaining non-complexed label in the control zone.

The accumulation of visible labels may be assessed either visually or by optical detection devices. Retention of labels in the capturing zone indicates the presence of target analyte in the sample. Retention of label in the control zone indicates that sufficient fluid has flow passed the labeled and capturing zones and that the labeled reagent is not denatured or degraded due to storage, buffer composition and sample composition, etc., and the assay is valid.

In addition, the visible intensity of the accumulated labels may be correlated with the concentration or titer (dilution) of analyte in the patient sample. The correlation between the visible intensity of accumulated labels and analyte concentration may be made by comparison of the visible intensity to a reference standard. Thus the analyte levels may be determined by devices of the present invention.

Figure 2:
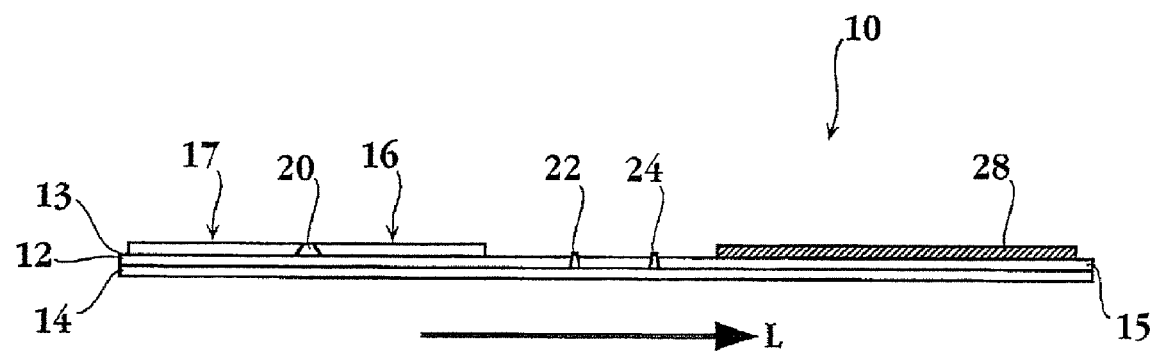
FIG. 2 shows the side elevation view of the test strip of FIG. 1.

FIGS. 1 and 2 show a test strip 10, which is an embodiment of the device of the invention, useful for performing the assay method of the present invention. Test strip 10 includes an elongated porous matrix 12 supported by a solid support 13 and having upstream and downstream ends 14, 15, respectively. A porous-material pad 16 is disposed on an upstream portion of the matrix 12. This pad includes a sample-loading or sample-receiving zone or region 17 on which a sample containing adhesin peptide is applied to the strip, and downstream of the sample-loading zone, a reaction region or zone 20 containing a mobile, reporter-labeled anti-adhesin antibody.

As seen in FIG. 2, pad 16 is attached to the upper surface of matrix 12, and communicates therewith by capillary fluid flow. Thus, sample fluid applied to the sample-application pad flows into pad 16, through pad 16 into the reaction region. Here sample fluid causes release of the mobile antibody into solution, where it reacts with sample adhesin, forming a mobile adhesin-labeled complex that can migrate through the pad and into matrix 12, by capillary flow through the pad and adjoining matrix.

Matrix 12, in turn includes a detection zone 22 where a stripe of capture reagent has been deposited and control zone 24 where a stripe of control reagent has been deposited. In this illustrated embodiment, the capture reagent and control reagent are deposited as stripes crossing the width of elongated matrix 12. However, it is understood that the capturing and control reagents may be deposited in any suitable format.

Covering matrix 12 at its downstream end is an absorbent pad 28. A tape cover over the absorbent pad 28 provides a gripping surface or handle for the test strip. The purpose of pad 28 is to serve as an absorbent reservoir, to continue to draw sample fluid from the application zone through the detection and control zones.

Matrix 12 is composed of a glass fiber filter paper that allows a sample received at sample receiving zone 17 to flow by capillary action along the longitudinal axis of test strip 10. Other porous material, such as the non-bibulous matrix materials described above may also be used. Solid support 13 is formed of a nitrocellulose membrane. Other suitable materials, such as paper, nylon membranes, glass, plastic, metal, and the like may also be used.

In one specific embodiment, test strip 10 is designed for the detection of adhesin protein AP65 of *T. vaginalis* (analyte), the detection zone in striped gold conjugated rabbit anti-AP65 IgG and the capturing zone is striped with anti-AP65 IgG. An exemplary procedure of producing test strip 10 is described in Examples 1 to 6.

Figure 3:
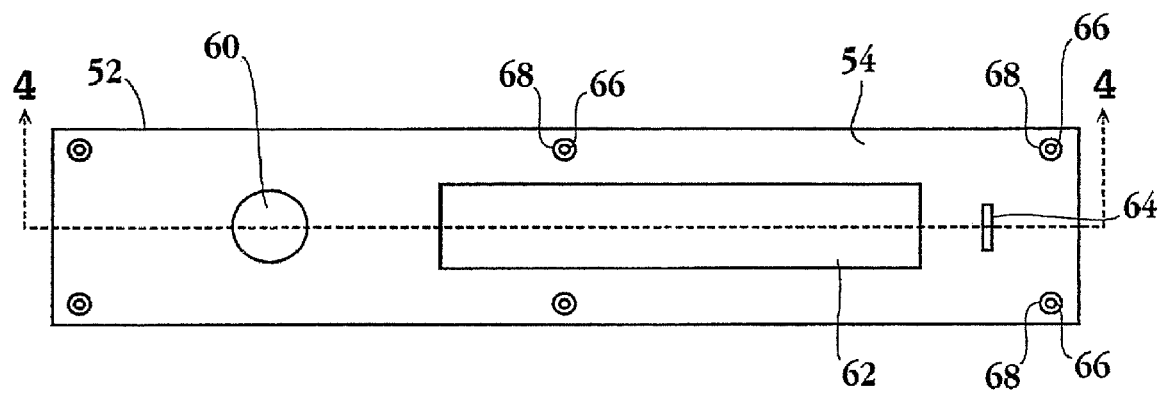
FIG. 3 is a plan view of an assay kit in accordance with the invention.
Figure 4:
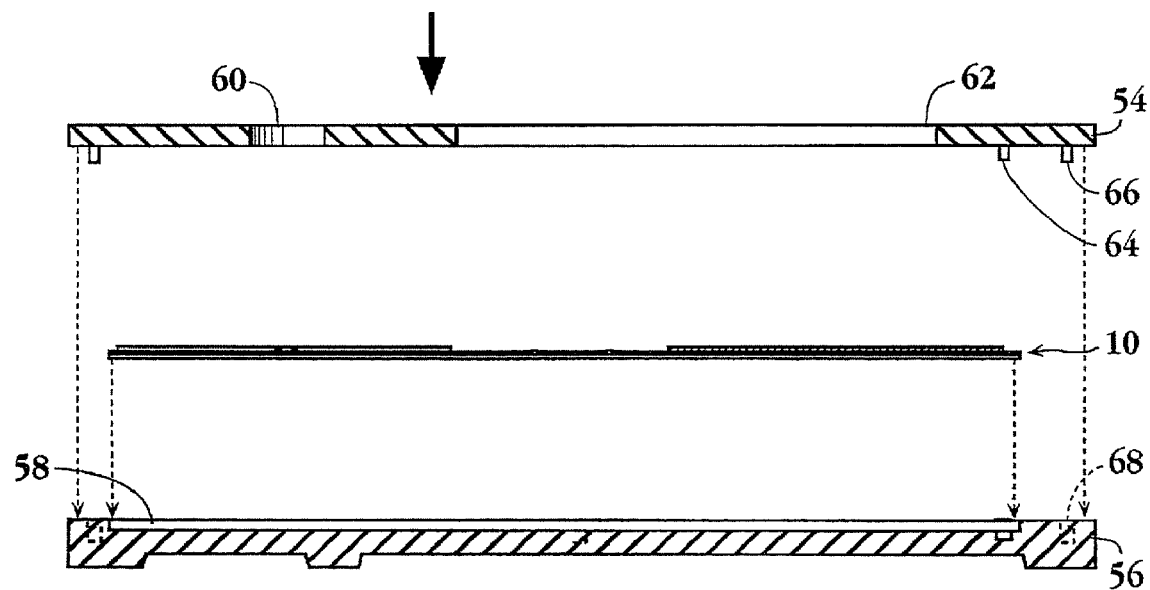
FIG. 4 is a sectional side view of the kit in FIG. 3.

Test strip 10 may be housed within a housing to facilitate handling of the strip. FIGS. 3 and 4 illustrate a test-strip cassette 50, which includes a test strip 10 enclosed within a housing 52. Housing 52 is designed to allow easy griping by the person performing the assay. Housing 52 is composed of top and bottom portions 54 and 56, respectively. Bottom portion 56 contains a well 58 for receiving test strip 10 therein. Top portion 56 includes two windows 60 and 62. Window 60 is adapted for receiving a fluid sample. Window 62 is for viewing the result of the assay. Provided in top portion 54 is a peg 64 which is aligned over well 58, for anchoring the test strip in the well. The two portions are held together in alignment by corner pins, such as pin 66 in portion 54, received in corresponding holes, such as hole 68, in portion 56.

Housing 52 may be constructed of any water resistant materials that are of adequate strength, e.g., any plastic material, such as polyethylene, polypropylene, polystyrene, and the like. If a plastic material is used, housing 52 may be produced by any conventional molding techniques.

Cassette 50 can be easily assembled by first placing a test strip 10 in well 58 of bottom portion 56. Top portion 54 is then placed against the bottom portion, with window 60 being aligned with sample-loading zone 17 and window 62 being aligned with detection (capture) and control zones 22, 24, peg 64 being in contact with absorbent pad 28. The two portions can then be snapped together, through interfitting pins and openings.

The kit of the invention may include a single assay strip as described above, or a plurality of the test strips. The plurality of strips may be designed for duplicative testing or for testing for the presence or absence of different *Trichomonas* species, isolates or drug resistant markers, or designed to test for a panel of additional disease agents such as other STDs (*Chlamydia*, for example), or other vaginitis causing agents (*Candida* yeast and *Gardnerella* bacteria, for example), or multiple devices capable of detecting several animal *Trichomonas* species. The kit may include sampling tools, e.g., sterile cotton swabs for obtaining an endocervical sample, and sample filtration and concentration apparatus. The kit may also include sample preparation solutions, e.g., buffers for neutralizing the samples or for extracting/solubilizing the *Trichomonas* antigen into solution. Other materials useful in the performance of the assays can also be included in the kits, including test tubes, transfer pipettes, and the like. The apparatus and reagents includes vary depending on the types of tests performed and are generally within the knowledge of those skilled in the art.

In one preferred embodiment, the kit is for the detection of *T. vaginalis*. The device includes a gold conjugated antibody DM116 raised against the AP65 family of adhesin proteins contained within the detection zone, and a C55 antibody or a fragment thereof, that specifically binds to an AP65 epitope distinct from that bound by DM116, immobilized within the capturing zone. In another preferred embodiment, the kit includes a buffer solution having a pH of about 4.0 to about 9.0. Preferably, the buffer is a sample dissolving buffer containing about 0.5% Triton X-100 and 0.1% BSA in double distilled water. The device, solution reagents, containers and sampling tools will generally be included together and packaging of the type conventional for immunoassay kits, e.g., boxes, bags, cylinders, shrink wrap cards, and the like. Optionally, the kit may further include written instructions setting forth the method step of the present invention. Any of a number of standard aqueous buffer solutions, such as phosphate, Tris, or a buffer containing Triton X-100, BSA and distilled water, at pH between about 4.0 to about 9.0 can be used to prepare the biological sample for analysis. The selection of a suitable buffer is within the knowledge of those skilled in the art.

Where the urine is the biological sample, the sample may be native urine, a fractionated portion of native urine, or otherwise treated, e.g., by filtration, either in a concentrated form or diluted form. An exemplary device for the optimal, single step filtration and testing of urine test samples contains a filter substrate that serves as the support medium for the test and control antibodies. The antigen or antigen/labeled antibody complex is contacted as the liquid is passed over and through the filter substrate. Such flow through diagnostic devices are known to those practiced in the art and this method is consistent with the method of this invention. Any number of buffer solutions may be used to dilute the native urine, with Triton X-100 or phosphate buffers at pH between about 4.0 to about 9.0 being preferred. The liquid fraction and the particulates fraction of native urine may be separately analyzed. The two fractions of the native urine may be separated by any of the solid-liquid separation methods known to the art, such as, sedimentation, centrifugation, or filtration and liquid and particulates are separately collected. The particulates may then be re-suspended in buffer, e.g., in a Triton X-100 buffer solution to solubilize or extract the analyte protein of interest. The suspension can then be analyzed for the presence of the analyte. The liquid fraction of the separated urine may be analyzed as is, or pretreated before analysis. The pretreatment may include concentration, dilution or neutralization.

In another embodiment where a vaginal swab is the biological sample, the biological fluid contained in the swab is first solubilized and extracted into a buffer solution. An exemplary extraction procedure is described in Example 4. A preferred buffer includes 0.5% Triton X-100, 0.1% BSA, and double distilled water. Any other buffer solutions, e.g., phosphate buffers having pH ranges between 4 to 9 may also be used.

The prepared fluid sample (urine or vaginal swab) is then applied to one of the devices of the invention, e.g. test strip 10 or test cassette 50 (FIGS. 1 and 3). If a test strip is used, the strip may be used as a dipstick to draw up the sample fluid. If a test cassette 50 is used, the sample fluid may be transferred using a pipette and be placed in the sample receiving window 60. The fluid received flow along the porous matrix under capillary action towards the detection zone, the capture zone and the control zone. The result of the test can be read directly from the labels captured in the capturing zone and the control zone. A colored (red, if the label is colloidal gold) line at the capture zone and the control zone indicates a positive result for the detection of *Trichomonas* infection. A color line at the control zone only indicates a negative result and the test is invalid. No line indicates the test is invalid.

From the foregoing, it will be appreciated how various objects and features of the invention are met. The assay is simple, rapid, and easily adapted to a doctor's office or home setting. According to an important feature of the invention, the assay is highly sensitive, picking up virtually all positives in human subjects infected with *T. vaginalis* (see Examples 4 and 5 below). The performance characteristic of an embodiment of the assay of the invention for the detection of *T. vaginalis* infection was determined from a composite reference standard sample set (CRS). This set of sample is a collection of vaginal specimens from 206 patients presenting with symptoms of vaginitis. The specimens were tested for the presence of T vaginalis by wet mount microscopy and the device of the invention. The discrepancy between the two assays were resolved by the culture method (In-pouch-Tv™ culture, BioMed, Inc., San Jose, Calif.).

It has been demonstrated that the assay, embodied in the test device of the invention, identified all wet mount positive patients (75) as tested positive and identified 21% of wet mount negative patients (28/131, confirmed by culturing method) also as tested positive with *T. vaginalis*. The sensitivity of the assay is reported at approximately 100%. The overall specificity of the assay is reported at 98%. The ability to achieve such high sensitivity and specificity using a detection protocol could not have been predicted prior to the work reported in the present application. The results are detailed in Example 5.

Moreover, the advantages features of the assay are seen employing urine as the body-fluid sample, allowing convenient and private sample collection, and assay determination for both men and women. Similarly, the immunoreactive reagents of the assay are readily applicable to a pap smear test, or the residual fluids from a pap smear test, allowing the assay to be included in one or more other assays that are normally performed as part of a pap smear. Further, the immunoreactive reagents of the assay are readily applicable to other rapid test formats, such as the flow through type of tests in which the sample flows through a membrane or filter substrate.

The following examples describe specific aspects of the invention to illustrate the invention and also provide a description of methods that can be used to identify and test the presence of *Trichomonas* in a sample, and to aid those of skill in the art in understanding and practicing the invention. The examples should not be construed as limiting the invention in any manner.

EXAMPLE 1

Purification of Monoclonal Antibody

Monoclonal anti-*Trichomonas* antibodies (Mabs) were prepared as described in U.S. Pat. No. 4,707,442 to Alderete. The Mabs were purified either from culture supernatant or ascites by protein A-Sepharose chromatography (Goding, J Immunol Meth (1976) 42:17) (Pharmacia LKB). About 2 to 6 mL of ascites fluid produced from the appropriate hybridoma was diluted 1:1 with Binding Buffer containing 1.5M glycine, 3 M NaCl adjusted to pH of about 8.9. The DM116 Mab ascites were subjected to dialysis with binding overnight at room temperature. The dialysed Mab ascites were eluted from the protein A-Sepharose CL-4B affinity gel chromatography column with the Binding Buffer at a rate of 0.5 mL/minute. Elution was monitored by determining the absorbance of each sample at 280 nm, and the column was washed until the absorbance was below 0.001 O.D. Then, IgG was eluted from the column using 0.1 M citric acid buffer adjusted to an approximate pH 4.0. Elution of immunoglobulin was monitored by determining the absorbance of each sample at 280 nm.

EXAMPLE 2

Preparation of Monoclonal Antibody Gold Conjugate

A flask containing 100 ml, of ultra-pure water was heated to about 80-85° C. Then, with gentle stirring, 1 mL of 1% AuCl (2×0.5 mL) and 1.75 mL of 1% sodium citrate solution (2×0.5, and then 0.75 mL aliquots) were consecutively added to the hot water. The solution was further heated at 80-85° C. until the color changes from slightly yellow to purplish black to cherry wine.

In a glass tube, to 10 mL of the 1:1.75 gold solution prepared as above was added 200 μL of freshly prepared 100 mM of carbonate (100 mM). The solution was vortexed for 3 seconds. Then 300 μL of DM116 IgG (1 m/mL) was added, and the solution was vortexed for 3 seconds again. The tube was incubated for 30 min. at room temperature, 100 μL of the conjugate blocking solution was added with vortexing for 3 seconds, followed by centrifugation at 8000 rpm for 30 min. The centrifuge was allowed to come to a complete stop without the use of the breaking system. The conjugate blocking solution consists of about 25 mM potassium phosphate (pH 7.4-7.6), about 5% bovine serum albumin and about 0.10% sucrose. The supernatant was aspirated off to give a residual volume of about 300 μL. The concentrated conjugate is then transferred to a new container, and its volume is determined. The concentrated conjugate is diluted to a 10× concentration by adding the conjugate resuspension solution. The conjugate resuspension solution contains 25 mM potassium phosphate (pH 7.4-7.6), 1% bovine serum albumin and about 0.10% sucrose. The amount of conjugate resuspension solution to be added was determined by dividing the total volume of the gold solution by (10—the volume of the concentrated conjugate that is transferred to the new container). The monoclonal antibody gold conjugate can be stored in a refrigerator, preferably at about 2-8° C., until use.

EXAMPLE 3

Preparation of Assay Dry Strip

A. Addition of Immobilized Antibodies to Dry Strip

A preparation of 1 mg/mL of the rabbit anti-*T. vaginalis* IgGs was dialyzed overnight at room temperature against the coating buffer consisting of 50 mM carbonate-bicarbonate buffer at pH 9.6. The IgGs were then loaded onto the X-Y-Z Dispensing Platform (BIO.DOT INC.), and the machine was programmed to deliver 1 μL/cm of the liquid onto a nitrocellulose membrane. The membrane was then dried at room temperature to 37° C. for about 3 h. The blocking buffer (0.5% BSA; 4% sucrose in PBS) was then sprayed over the membrane, and the membrane was dried overnight at room temperature. The membrane was stored at about 2-8° C. in the absence of moisture.

B. Application of Gold Conjugate DM116 Antibody at the Reaction Zone

A glass fiber filter paper was submersed into the gold pad pre-treatment buffer (0.5% (w/v) poly alcohol; 0.71% (w/v) di-sodium phosphate; 0.1% (v/v); Triton X-100; 0.5% BSA (w/v); DDW; pH 7.4). The glass fiber filter paper was dried in either a 40-50° C. oven for about 3 hours, or was air dried overnight. The gold conjugate DM116 antibody was then applied onto the treated glass fiber filter paper, followed by either air drying overnight at room temperature or drying in a 37° C. oven until the pad appears dry. The pad was stored at about 2-8° C. in the absence of moisture.

C. Assembly of the Test Strip

On the antibody coated nitrocellulose membrane prepared in part A. was placed a strip of Whatman/Gelman filter paper (2.5 cm×30.0 cm) such that the two overlapped by 1 mm at the top. Then the gold conjugate pad prepared in part B. was placed such that it overlapped by 1 mm at the bottom. The bottom 1 mm of the gold conjugate pad was overlaid with a second strip of the Whatman/Gelman filter paper. The assembly was kept in place by covering with a layer of adhesive plastic tape. The assembly is then cut in smaller strips of approximately 2 mm width, and stored at about 2-8° C. in the absence of moisture.

EXAMPLE 4

Test Procedure and Results

The test procedure using the test strip of the invention is as follows:

1. Use sterile cotton swab to collect testing sample from patient's vaginal tract. Process the swab as soon as possible after collecting the specimen. However, because the assay of the invention does not require live organisms for processing, the sample swab may be stored and transported in a dried form. The swab may also be stored at 2-8° C. for up to 24 hours prior to extraction and testing. Alternatively, the swab may be extracted and the extracted specimen stored at 2-8° C. for up to 24 hours.

2. Dip the swab in to approximately 1 mL of the sample dissolving buffer (0.5% Triton X-100; 0.1% BSA; DDW). Vigorously mix the solution by rotating the swab forcefully against the side of the container at least ten times (while submerged). Test results are obtained when the specimen is vigorously extracted in the solution. Allow the swab to soak in the sample buffer for one minute prior to mixing again. Express as much liquid as possible from the swab by pressing it against the side of the tube and rotating as the swab is withdrawn. Discard the swab.

3. Insert dipstick test strip prepared in example 7 in to the vial of mixture sample solution.

4. Read results at 10 minutes (some positive results may be seen earlier. If the test appears to be negative after ten minutes, wait a further 10 minutes for all background color to dissipate before confirming test result.

5. A red line, even with uneven color shading, is considered a valid result. In case of moderate or high positive specimens, some red color behind the Test Line may be seen. As long as the Test Line and the Control Line are visible, the results are valid. The results are interpreted as follows:

Two lines—positive. A red Test Line and a red Control Line is a positive result for the detection of *Trichomonas* antigens. Note that the red line can be any shade of color.

One line—negative. A red Control Line but no red Test Line is a presumptive negative result.

No lines—test invalid. If no red Control Line appears or background color make reading the red Control Line impossible, the result is invalid.

The performance characteristic of the assay of the invention was determined from a composite reference standard sample set (CRS). This set of sample is a collection of vaginal specimens from 206 patients presenting with symptom of vaginitis. The specimens were tested from *Trichomonas* by wet mount microscopy and the assay of the invention. The discrepancy between the two methods were resolved by the culture method (In-pouch-Tv™ culture, BioMed, Inc., San Jose, Calif.) See, Alonzo and Pepe (1999).

For the total of 206 samples in the composite reference standard, 75 are identified positive and 131 is identified negative by wet mount. The device of the invention identified all wet mount positive samples (75) as positive and 101 wet mount negative samples as negative. The device however, identified the remaining wet mount negative samples as positive for the presence of *T. vaginalis*.

The 131 wet mount negative samples were further analyzed by the culture method in order to resolve the discrepancy between the wet mount method and the device of the invention. It is found that out of the 30 samples that were judged wet mount negative, but positive by the assay of the invention, 28 are found positive and 2 are found negative by the culture method in addition, it is found that the 101 samples that are negative by both the wet mount method and the assay of the invention are also negative by the culture method. The result is tabulated in Table 1 below.

TABLE 1

XENOSTRIP-TV COMPARED TO WET MOUNT MICROSCOPY AND RESOLVED BY CULTURE

| N = 206 | WSet Mount (WM) | | Resolve WM (−) samples (n = 131) | |
|---|---|---|---|---|
| | (+) | (−) | Culture (c) (+) | Culture (c) (−) |
| XenoStrip-Tv$^T$ (+) | 75 | 30 | 28 | 2 |
| XenoStrip-Tv$^T$ (−) | 0 | 101 | 0 | 101 |

The performance of the assay of the invention compared to wet mount microscopy and resolved by culture is as follows:

$$\text{Sensitivity } XenoStrip\text{-}Tv^{TM} = X(+)WM(+) + X(+)WM(-)C(+)/$$
$$X(+)WM(+) + X(+)WM(-)C(+) +$$
$$X(-)WM(+) + X(-)WM(-)C(+)$$
$$= 75 + 28/75 + 28 + 0 + 0$$
$$= 103/103$$
$$= 100.0\%(Cl\ 100\% - 100\%)$$

$$\text{Specificity } XenoStrip\text{-}Tv^{TM} = X(-)WM(-)C(-)/X(-)WM(-)C(-) +$$
$$X(+)WM(-)C(-)$$
$$= 101/101 + 2$$
$$= 101/103$$
$$= 98.1\%(Cl\ 95.4\% - 100\%)$$

$$NPV\ XenoStrip\text{-}Tv^{TM} = X(-)WM(-)C(-)/X(-)WM(-)C(-) +$$
$$X(-)WM(+) + X(-)WM(-)C(+)101/$$
$$101 + 0 + 0$$
$$= 101/101$$
$$= 1.000(Cl\ 1.000 - 1.000)$$

$$PPV\ XenoStrip\text{-}Tv^{TM} = X(+)WM(+) + X(+)WM(-)C(+)/$$
$$X(+)WM(+) + X(+)WM(-)C(+) +$$
$$X(+)WM(-)C(-)$$
$$= 75 + 28/75 + 28 + 2$$
$$= 103/105$$
$$= 0.981(Cl\ 0.955 - 1.000)$$

The antibody reagents used for the assay of the invention have been shown to be unreactive with normal vaginal flora, other sexually transmitted agents (including *Gardnerella vaginalis* and *Candida* species), and urogenital samples from normal uninfected individuals.

The antibody device of the invention detected soluble antigen present in vaginal swab-derived material from 10-1000 organisms, a lower concentration than expected from discharge of patients.

The result of the analysis by wet mount microscopy was compared to culture and the performances of the methods, culture relative to wet mount and wet mount relative to culture are tabulated in Tables 2 and 3, respectively.

TABLE 2

COMPARISON OF WET MOUNT MICROSCOPY TO CULTURE

| N = 206 | Culture | | Performance of Wet Mount versus Culture |
|---|---|---|---|
| | (+) | (−) | |
| Wet Mount (WM) (+) | 66 | 28 | Sensitivity = 70.2% |
| Wet Mount (W) (−) | 28 | 103 | Specificity = 95.4% |

TABLE 3

COMPARISON OF CULTURE TO WET MOUNT MICROSCOPY

| N-206 | Culture | | Performance Culture versus Wet Mount |
|---|---|---|---|
| | (+) | (−) | |
| Culture (C) (+) | 66 | 28 | Sensitivity = 88.0% |
| Wet Mount (WM) (−) | 28 | 103 | Specificity = 78.6% |

Table 4 compares the performance of the assay of the invention to culture and wet mount microscopy.

TABLE 4

COMPARISON[‡] OF XENOSTRIP-TV ™ TO CULTURE AND WET MOUNT MICROSCOPY

| N = 206 | Sensitivity | Specificity | PPV | NPV | Accuracy |
|---|---|---|---|---|---|
| Culture | 88.0% | 78.6% | 0.702 | 0.920 | 82.0% |
| Wet Mount | 70.2% | 92.0% | 0.981 | 1.000 | 99.0% |
| XenoStrip-Tv | 100.00% | 98.1% | 0.981 | 1.000 | 99.0% |

[‡]values are CRS for XenoStrip-Tv ™. Culture relative to wet mount, and wet mount relative to culture.

EXAMPLE 5

Additional Testing

An evaluation of the assay and device of the invention was conducted at three physician offices. Testing at each site was conducted by personnel of diverse educational backgrounds. Each site tested a randomly coded panel of negative (3), low positive (3), medium positive (3), and high positive (3) samples. The test results obtained had a 100% agreement with the expected results.

While the preferred embodiment of the invention has been illustrated and described, it will be appreciated that various changes can be made therein without departing from the spirit and scope of the invention.

REFERENCES

Alderete et al., *Infect. Immun.*, 40:284-291, 1983
Alderete et al., *Infect. Immun.*, 49:463-468, 1985.
Alderete et al., *Infect. Immun.*, 52:70-75, 1986
Alderete et al., *Infect. Immun.*, 53:285-293, 1986.
Alderete et al., *Infect. Immun.*, 53:697-699, 1986.
Alderete et al., *Infect. Immun.*, 55:1037-1041, 1987
Alderete and Garza, *Infection and Immunity*, 56(1):28-33, 1988.
Alderete and Garza, *Infection and Immunity*, 56(10):2256-2562, 1988.
Alonzo and Pepe, *Statistics in Medicine*, 18:2987-3000, 1999.
Arroyo et al., *Molecular Microbiology*, 6(7):853-862, 1992.
Arroyo et al., *Arch Med Res* 26(4):36-369, 1995.
Arroyo et al., *Molecular Microbiology*, 7(2):299-309, 1993.
Cuatrecasas, *J. Biol. Chem.*, 245:3059, 1970.
Lehker et al., *Journal of Exp. Med.*, 174:311-318, 1991.
van Der Schee C., et al. *J. Clin Microbiol.* 1999 December: 37 (12) 4127-30
Wasserheit, J. N., *Sex. Trans. Dis.*, 19:61-77, 1992.
Yap et al., *Genitouria. Med,* 71:402-404, 1995.
Zhang et al., *Ann. Epidemol.*, 5:325-332, 1995.

The invention claimed is:

1. A method for detecting *Trichomonas vaginalis* infection in a human subject, comprising:

a) applying a sample from a site of infection in the subject to a sample application zone at a first end of a dry-strip, whereby the sample moves by capillary action along the dry-strip toward a second end, thereby first passing through a reaction zone comprising a first monoclonal antibody specific against a *Trichomonas vaginalis* adhesin protein epitope and then passing through a detection zone comprising a second monoclonal antibody specific against a *Trichomonas vaginalis* adhesin epitope, wherein said first and second monoclonal antibodies were present on the test strip prior to application of the sample and wherein said first and second monoclonal antibodies are specific for different epitopes on the same *Trichomonas vaginalis* adhesin protein, under conditions whereby an antigen/antibody complex will form if the subject is infected with *Trichomonas vaginalis*; and b) detecting the presence of said complex, whereby the presence of said complex detects *Trichomonas vaginalis* infection in said subject.

2. The method of claim 1, wherein said first and second monoclonal antibodies, respectively, are specific against an epitope of an adhesin protein selected from the group consisting of AP65 adhesin protein, AP51 adhesin protein, AP33 adhesin protein, and AP23 adhesin protein.

* * * * *

UNITED STATES PATENT AND TRADEMARK OFFICE
CERTIFICATE OF CORRECTION

PATENT NO. : 7,648,829 B2  
APPLICATION NO. : 11/931488  
DATED : January 19, 2010  
INVENTOR(S) : Alderete et al.

Page 1 of 1

It is certified that error appears in the above-identified patent and that said Letters Patent is hereby corrected as shown below:

Title Page 2:

Col. 2, Other Publications, Line 11, "Cogne et al.": Please correct "Jpurnal" to read -- Journal --

Signed and Sealed this

Twentieth Day of April, 2010

David J. Kappos  
*Director of the United States Patent and Trademark Office*